United States Patent [19]

Bertram et al.

[11] Patent Number: 5,466,827
[45] Date of Patent: Nov. 14, 1995

[54] USE OF THIOALKANEDIONES AS AROMA SUBSTANCES

[75] Inventors: Heinz-Jürgen Bertram; Roland Emberger; Matthias Güntert, all of Holzminden; Peter Werkhoff, Höxter, all of Germany

[73] Assignee: Haarmann & Reimer GmbH, Holzminden, Germany

[21] Appl. No.: 128,440

[22] Filed: Sep. 28, 1993

[30] Foreign Application Priority Data

Oct. 5, 1992 [DE] Germany ............... 42 33 350.4

[51] Int. Cl.$^6$ ............... C07D 333/32; C07D 307/02; C07C 319/00; C07C 49/105
[52] U.S. Cl. ............... 549/66; 549/62; 549/78; 549/478; 568/42; 568/308; 568/375; 568/376
[58] Field of Search ............... 549/475, 479, 549/78, 62, 66; 568/42, 308, 375, 376

[56] References Cited

U.S. PATENT DOCUMENTS

| | | | |
|---|---|---|---|
| 3,872,111 | 3/1975 | Evers et al. | 549/479 |
| 3,883,572 | 5/1975 | Helmlinger et al. | 568/42 |
| 3,891,710 | 6/1975 | Evers et al. | 549/479 |
| 3,988,510 | 10/1976 | Evers et al. | 549/479 |
| 4,055,578 | 10/1977 | Evers | 549/475 |
| 4,107,184 | 8/1978 | Evers et al. | 549/479 |
| 5,145,703 | 8/1992 | Emberger et al. | 549/475 |

OTHER PUBLICATIONS

Recent Developments in Flavor and Fragrance Chemistry, R. Hoppe, K. Mori Eds. VCH Verlagsgesellschaft Weinheim (1993).
CA, vol. 73:55474v (1970).
CA, vol. 57:3385i (1962).
CA, vol. 49:1696h (1955).
The Chemical Society of Japan, 1987, pp. 2227–2228.
J. Am. Chem. Soc. 1982, 104, 2655–2657.
Synthesis, Jun. 1991, 487–490.
Journal of Chemical Research, Synopses 1988 Issue 11 (Nov. 1988).

*Primary Examiner*—Richard L. Raymond
*Assistant Examiner*—Deborah Lambkin
*Attorney, Agent, or Firm*—Sprung Horn Kramer & Woods

[57] ABSTRACT

Thioalkane α,β-diketones have interesting organoleptic properties and are therefore suitable as aroma substances.

5 Claims, No Drawings

USE OF THIOALKANEDIONES AS AROMA SUBSTANCES

The invention relates to the use of compounds of the formula

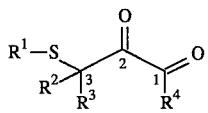

wherein $R^1$ denotes $C_1$–$C_{12}$-alkyl, $C_2$–$C_{12}$-alkenyl, $C_2$–$C_{12}$-alkinyl, $C_3$–$C_{12}$-cycloalkyl, $C_6$–$C_{12}$-ar-$C_1$–$C_6$-alkyl, preferably benzyl, optionally substituted $C_6$–$C_{12}$-aryl, preferably phenyl, a 5- or 6-membered heterocyclic radical with oxygen, sulphur and/or nitrogen as the hetero atom and with 0 to 3 double bonds, which can be substituted by 1 to 3 $C_1$–$C_3$-alkyl groups, or heterocyclo-methyl, $R^2$ denotes hydrogen or $C_1$–$C_4$-alkyl and $R^3$ and $R^4$ independently of one another denote hydrogen, $C_1$–$C_8$-alkyl, $C_2$–$C_8$-alkenyl, $C_2$–$C_8$-alkinyl, $C_5$–$C_{12}$-cycloalkyl or $C_6$–$C_{12}$-aryl, preferably phenyl, or $R^2$ and $R^3$ together or $R^3$ and $R^4$ together denote a divalent radical which, with the C atom 3 or with the C atoms 1, 2 and 3, forms a 5- to 7-membered, preferably a 5- to 6-membered ring containing 0 to 2 hetero atoms from the series comprising nitrogen, oxygen and sulphur.

The term "alkyl" represents straight-chain or branched alkyl and includes, for example, methyl, ethyl, n- and i-propyl, n-, sec-, i- and tert-butyl, n-, i- and tert-pentyl, n-hexyl, i-octyl, i-nonyl, n-decyl and n-dodecyl.

The term "alkenyl" represents straight-chain or branched alkenyl and includes, for example, vinyl and allyl.

The term "alkinyl" represents straight-chain or branched alkinyl and includes, for example, ethinyl and propargyl.

The term "cycloalkyl" includes, for example, cyclopropyl, cyclobutyl, cyclopentyl, cyclohexyl and cycloheptyl.

"Aralkyl" preferably contains 1 to 6, in particular 1 to 4 C atoms in the straight-chain or branched alkyl part and preferably 6 to 12 C atoms, in particular phenyl or naphthyl, as the aryl part. Examples of such aralkyl groups include benzyl, 2-phenethyl and α- and β-naphthylmethyl.

The term "aryl" includes, for example, phenyl or naphthyl, in particular phenyl.

Substituents which are suitable for substituted aryl radicals include, for example, halogen, cyano, nitro, hydroxyl, amino, mercapto, straight-chain or branched halogenoalkyl having 1 to 6 carbon atoms and 1 to 13 identical or different halogen atoms, in each case straight-chain or branched halogenoalkylthio or halogeno-alkoxy having in each case 1 to 6 carbon atoms and in each case 1 to 13 identical or different halogen atoms, in each case straight-chain or branched alkenyl or alkinyl having 2 to 6 carbon atoms, in each case straight-chain or branched alkenyloxy or alkinyloxy having 2 to 6 carbon atoms, cycloalkyl having 3 to 8 carbon atoms, phenyl, phenoxy, phenylthio and phenylalkylthio or phenylalkoxy having in each case 1 to 4 carbon atoms in the straight-chain or branched alkyl part.

Preferred possible heterocyclic radicals $R^1$ are furyl, di- and tetrahydrofuryl, thienyl and di- and tetrahydrothienyl, which can be substituted by up to 2 $C_1$–$C_3$-alkyl groups.

The term "heterocyclo-methyl" is understood as meaning those radicals which are composed of a heterocyclic radical (defined above) a methylene group —$CH_2$—. In this context, "pyrrylmethyl" thus denotes the $R^1$ radical listed below under number 19.

If $R^2$ and $R^3$ together form a divalent radical, preferred possible radicals are 1,4-butylene and 1,5-pentylene.

If $R^3$ and $R^4$ together form a divalent radical, preferred possible radicals are 1,2-ethylene and 1,3-propylene, it being possible for these radicals to be substituted by 1 or 2 methyl groups.

Preferred compounds of the formula (I) are listed below in tabular form:

| Number | $R^1$ | $R^2$ | $R^3$ | $R^4$ |
|---|---|---|---|---|
| 1 | Phenyl | H | $CH_3$ | $CH_3$ |
| 2 | Phenyl | H | $C_2H_5$ | $C_2H_5$ |
| 3 | Phenyl | H | 1,2-ethylene | |
| 4 | Phenyl | H | 1,3-propylene | |
| 5 | Benzyl | H | $CH_3$ | $CH_3$ |
| 6 | Benzyl | H | 1,3-propylene | |
| 7 | 2-furyl | H | $CH_3$ | $CH_3$ |
| 8 | 5-methyl-2-furyl | H | 1,3-propylene | |
| 9 | 2-thienyl | H | 1,3-propylene | |
| 10 | 5-methyl-2-thienyl | H | 1,3-propylene | |
| 11 | 2-furylmethyl | H | $CH_3$ | $CH_3$ |
| 12 | 2-furyl (3-ethyl) with $CH_2$— | H | $C_2H_5$ | $C_2H_5$ |
| 13 | 2-furyl with $CH_2$—/$C_2H_5$ | H | $C_2H_5$ | $C_2H_5$ |
| 14 | 3-methyl-2-furylmethyl | H | $C_2H_5$ | $C_2H_5$ |
| 15 | 3-ethyl-2-thienylmethyl | H | $C_2H_5$ | $C_2H_5$ |
| 16 | 3-methyl-2-thienylmethyl | H | $C_2H_5$ | $C_2H_5$ |
| 17 | 2-thienyl | H | —$CH_2CH(CH_3)$— | |

-continued

| Number | R¹ | R² | R³ | R⁴ |
|---|---|---|---|---|
| 18 | 2-methylfuran-5-yl | H | —CH₂—CH(CH₃)— | |
| 19 | (1H-pyrrol-2-yl)methyl— | H | CH₃ | CH₃ |
| 20 | H₂C=CH—CH₂— | H | 1,3-propylene | |
| 21 | H₂C=CH—CH₂— | CH₃ | 1,3-propylene | |
| 22 | 5-methylfuran-2-yl | H | CH₃ | CH₃ |
| 23 | 5-methylfuran-2-yl | H | H | CH₃ |
| 24 | 5-methylthiophen-2-yl | H | CH₃ | CH₃ |
| 25 | 5-methylthiophen-2-yl | H | H | CH₃ |
| 26 | 5-methylfuran-2-yl | H | CH₃ | CH₃ |
| 27 | 5-methylfuran-2-yl | H | H | CH₃ |
| 28 | 5-methylfuran-2-yl | H | 1,3-propylene | |
| 29 | 5-methylfuran-2-yl | H | —CH₂—CH(CH₃)— | |
| 30 | 5-methylthiophen-2-yl | H | 1,3-propylene | |
| 31 | 5-methylthiophen-2-yl | H | —CH₂—CH(CH₃)— | |
| 32 | 3,5-dimethylfuran-2-yl | H | CH₃ | CH₃ |
| 33 | 3,5-dimethylfuran-2-yl | H | 1,3-propylene | |
| 34 | 3,5-dimethylthiophen-2-yl | H | CH₃ | CH₃ |
| 35 | 3,5-dimethylthiophen-2-yl | H | —CH₂—CH(CH₃)— | |
| 36 | pyridin-2-yl | H | 1,3-propylene | |
| 37 | pyridin-4-yl | H | —CH₂—CH(CH₃)— | |
| 38 | H₂C=CH—CH₂— | H | CH₃ | CH₃ |
| 39 | H₂C=CH—CH₂— | H | H | CH₃ |

The compounds 1 are new, apart from a few exceptions. The exceptions are 1-phenylthio-2,3-pentanedione (K. Mori et al., Synthesis 487 (1991)), 1-phenylthio-2,3-butanedione (T. Fujisawa et al., Chem. Lett. 2227 (1987)), and ethylthiomethylglyoxal and (2-hydroxyethyl)-methylglyoxal (J. W. Kozarich et al., J. Amer. Chem. Soc., 104, 2655 (1982)); the compounds are employed as starting substances for enzymatic reductions.

The invention thus furthermore relates to compounds of the formula (I) excluding the 4 known compounds.

The compounds (I) can be prepared, for example, by a) reaction of thiols of the formula

$$R^1—SH \qquad (II)$$

with ketones of the formula

wherein X designates a halogen atom, p-toluenesulphonate, methanesulphonate, acetyl or benzoyl, b) reaction of methyl thioethers of the formula

$$R^1—S—CH_3 \qquad (IV)$$

with the acetals of α-ketocarboxylic acid esters of the formula

wherein R⁵ represents methyl, ethyl, n-propyl, or iso-propyl, in the presence of strong bases, for example butyl-lithium (for deprotonation), and subsequent acetal cleavage (Synthesis 487 (1991)) or c) reaction of thioalkanediones of the formula

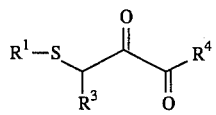

(VI)

with compounds of the formula

R²—X  (VII)

wherein X has the meaning given under a), in the presence of deprotonating agents,
wherein the substituents $R^1$ to $R^4$ in each case have the meanings given for the compounds (I) with the exception that $R^1$ in formula (IV) does not represent hydrogen.

The starting compounds for the preparation of the compounds (I) are known or can be prepared by processes analogous to known processes.

The processes for the preparation of the compounds (I) can be carried out with or without diluents. Suitable diluents are inert organic solvents, such as, for example, in particular, aliphatic, alicyclic or aromatic hydrocarbons, such as, for example, benzene, toluene, xylene, petroleum ether, hexane or cyclohexane, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide or N-methylformanilide, esters, such as ethyl acetate, or sulphoxides, such as dimethyl sulphoxide, or sulphones, such as sulpholane, alcohols, such as methanol, ethanol or isopropanol, or chlorinated hydrocarbons, such as chloroform or methylene chloride.

The processes for the preparation of the compounds (I) are preferably carried out in the presence of bases. Examples of suitable bases are alkali metal hydrides, hydroxides, amides, alcoholates, carbonates or bicarbonates, such as, for example, lithium diisopropylamide (LDA), sodium hydride, sodium amide, sodium hydroxide, sodium methylate, sodium ethylate, potassium t-butylate, sodium carbonate or sodium bicarbonate, or tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU), or oxides of alkaline earth metals, such as magnesium oxide or calcium oxide. The bases can be employed in an equimolar amount or in excess with respect to the thiol II employed or methyl thioether IV employed.

The temperatures for processes a) to c) can be varied within wide ranges. In general, the processes are carried out at temperatures between −100° C. and +100° C., preferably between −78° C. and +80° C., especially preferably between −78° C. and +50° C.

Working up of the reaction mixtures with isolation of the compounds (I) can be carried out by customary methods.

The invention thus furthermore relates to processes for the preparation of the new compounds (I).

The compounds (I) are useful aroma substances; they are distinguished by very low flavour threshold values. Thus, in a triangular test using 4-(2-methyl-3-furyl-thio)pentane-2,3-dione in 0.5% strength by weight aqueous sodium chloride solution, a test panel of 20 testers already found a significant difference between the zero sample and the sodium chloride solution containing only 5 ppb of 4-(2-methyl-3-furyl-thio)-pentane-2,3-dione. For 4-(2-methyl-3-furyl-thio)-butane-2,3-dione a test panel of 6 specially trained testers found a significant difference between the 0.5% strength by weight sodium chloride solution and the 0.5% strength by weight sodium chloride solution containing 5 ppb of 4-(2-methyl-3-tetrahydrofuryl-thio)-butane-2,3-dione.

The flavour descriptions for some of the compounds of the formula (I) according to the invention when used in 0.5% strength by weight aqueous sodium chloride solution are as follows:

4-(2-thienyl-thio)-pentane-2,3-dione: when added in an amount of 8 ppb: onion, garlic, cabbage 4-(2,5-dimethyl-3-thienylthio)-butane-2,3-dione: when added in an amount of 1 ppb: peach skin, fruity, meaty 4-(2,5-dimethyl-3-thienylthio)-pentane-2,3-dione: when added in an amount of 4 ppb: bread crust, grilled note, mustard note 4-(2-methyl-3-furyl-thio)-pentane-2,3-dione: when added in an amount of 0.8 ppm: roasted note, broth, yeast character, meaty 4-(2-methyl-3-furyl-thio)-butane-2,3-dione: when added in an amount of 75 ppb: meaty, hydrolysate 4-(2-methyl-3-thienyl-thio)-pentane-2,3-dione: when added in an amount of 8 ppb: meaty, roast note 4-(2-methyl-3-thienyl-thio)-butane-2,3-dione: when added in an amount of 8 ppb: beef broth, meaty, yeast character, sulphurous cis/trans-4-(2-methyl-3-tetrahydrofurylthio)-pentane-2,3-dione: when added in an amount of 0.5 ppm: roast note, meaty, broth The percentage data in the following examples relate to the weight, unless stated otherwise.

EXAMPLES

Example 1

1.12 g of potassium tert-butylate are suspended in 10 ml of dry tetrahydrofuran. 1 ml of 2-methyl-3-furanthiol is added dropwise at −20° C. under an inert gas atmosphere. The mixture is subsequently stirred at this temperature for 30 minutes. 1.64 g of 1-bromobutane-2,3-dione are then added dropwise at −20° C. The mixture is allowed to come to room temperature and is subsequently stirred for 2 hours. 20 ml of diethyl ether are then added, the mixture is subsequently poured onto 20 ml of water and the organic phase is separated off. The aqueous phase is extracted three times with 10 ml of ether each time, and the combined organic phases are washed with water and then dried over sodium sulphate.

After the solvent has been stripped off, 2.0 g of a pale yellow oil remain as a crude product.

The residue is purified by preparative high pressure liquid chromatography (HPLC; solvent: n-pentane). 1.1 g of 4-(2-methyl-3-furanyl-thio)-butane-2,3-dione (purity 93%) are obtained. The IR, NMR and mass spectra of the compound agree with the structure described for it.

Example 2

3 ml of dry tetrahydrofuran and 0.70 ml of diisopropylamine are initially introduced into the reaction vessel under an inert gas atmosphere. The mixture is then cooled to 0° C. and 2.66 ml of a 1.6 molar solution of butyl-lithium in hexane are added dropwise. The mixture is subsequently stirred at 0° C. for 10 minutes and is then cooled to −60° C. 0.99 g of 4-(2-methyl-3-furylthio)butane-2,3-dione, dissolved in 5 ml of dry tetrahydrofuran, is added dropwise very slowly at this temperature. When the addition has ended, the mixture is stirred at −60° C. for 30 minutes; during this operation, the colour of the solution changes from yellow to brown. 0.312 ml of methyl iodide is then added dropwise at −60° C. The mixture is then subsequently stirred at −60° C. for 30 minutes and at room temperature for 2 hours. It is poured onto water and extracted with diethyl ether. The aqueous phase is extracted three times with ether, and the combined organic phases are then washed with aqueous sodium bicarbonate solution and dried over sodium sulphate.

After the solvent has been stripped off, 0.9 g of a brown oil remain as the crude product.

The residue is purified by HPLC (solvent: n-pentane). 0.1 g of 4-(2-methyl-furylthio)-pentane-2,3-dione (purity 90%) is obtained. The IR, NMR and mass spectra of the compound agree with the structure described.

Example 3

1.0 g (8.6 mmol) of thiophene-2-thiol are dissolved in 8 ml of ether. 1.03 g (9.1 mmol) of potassium tert-butylate are added, while cooling at 0° C. When the addition has ended, the mixture is subsequently stirred at 0° C. for a further 15 minutes; 1.5 g (9.5 mmol) of 1-bromobutane-2,3-dione are then added. The mixture is allowed to warm to room temperature and is subsequently stirred for 4 hours; it is then poured onto water and extracted three times with ether. The combined organic phases are dried over sodium sulphate.

After the solvent has been stripped off, 720 mg of a brown oil remain.

The product is chromatographed for further purification. The mobile phase is initially n-hexane, and elution is then later carried out with a mixture of n-hexane/methyl tert-butyl ether (10:1 parts by volume). 0.2 g of 4-(2-thienyl-thio)-butane-2,3-dione (purity 90%) is obtained. The IR, NMR and mass spectra of the compound agree with the assumed structure.

We claim:

1. A method of imparting a meaty aroma to a material which comprises applying thereto an amount effective therefor of a compound of the formula

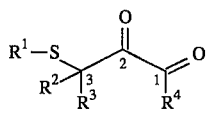 (I)

wherein $R^1$ denotes $C_1$–$C_{12}$-alkyl, $C_2$–$C_{12}$-alkenyl, $C_2$–$C_{12}$-alkinyl, $C_3$–$C_{12}$-cycloalkyl, $C_6$–$C_{12}$-ar-$C_1$–$C_6$-alkyl, optionally substituted $C_6$–$C_{12}$-aryl, thienyl and furyl which can be substituted by 1 to 3 $C_1$–$C_3$-alkyl groups; or thienyl and furyl methyl, $R^2$ denotes hydrogen or $C_1$–$C_4$-alkyl and $R^3$ and $R^4$ independently of one another denote hydrogen, $C_1$–$C_8$-alkyl, $C_2$–$C_8$-alkenyl, $C_2$–$C_8$-alkinyl, $C_5$–$C_{12}$-cycloalkyl or $C_6$–$C_{12}$-aryl or $R^2$ and $R^3$ together or $R^3$ and $R^4$ together denote a divalent alkylene radical which, with the C atom 3 or with the C atoms 1, 2 and 3, forms a 5- to 7-membered carbon ring.

2. The method according to claim 1, wherein such material is a foodstuff.

3. A compound of the formula

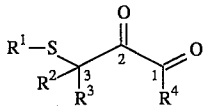

wherein $R^1$ denotes $C_1$–$C_{12}$-alkyl, $C_2$–$C_{12}$-alkenyl, $C_2$–$C_{12}$-alkinyl, $C_3$–$C_{12}$-cycloalkyl, $C_6$–$C_{12}$-ar-$C_1$–$C_6$-alkyl, optionally substituted $C_6$–$C_{12}$-aryl, thienyl and furyl which can be substituted by 1 to 3 $C_1$–$C_3$-alkyl groups; or thienyl and furyl methyl, $R^3$ and $R^4$ together denote a divalent alkylene radical which, with the C atom 3 or with the C atoms 1, 2 and 3, forms a 5- to 7-membered carbon ring.

4. The method according to claim 1, wherein such compound is 4-(2-methyl-3-furyl-thio)-butane-2,3-dione.

5. A compound according to claim 3, wherein such compound is 4-(2-methyl-3-furyl-thio)-butane-2,3-dione.

* * * * *